US010699356B2

(12) United States Patent
Thesman

(10) Patent No.: US 10,699,356 B2
(45) Date of Patent: Jun. 30, 2020

(54) SYSTEM AND METHOD OF PRIORITIZING AND ADMINISTERING HEALTHCARE TO PATIENTS HAVING MULTIPLE INTEGRAL DIAGNOSES

(71) Applicant: Debra Thesman, Rocklin, CA (US)

(72) Inventor: Debra Thesman, Rocklin, CA (US)

(*) Notice: Subject to any disclaimer, the term of this patent is extended or adjusted under 35 U.S.C. 154(b) by 0 days.

(21) Appl. No.: 14/447,183

(22) Filed: Jul. 30, 2014

(65) Prior Publication Data

US 2014/0343961 A1 Nov. 20, 2014

Related U.S. Application Data

(63) Continuation of application No. 13/754,693, filed on Jan. 30, 2013, now abandoned, which is a continuation of application No. 13/439,565, filed on Apr. 4, 2012, now abandoned, which is a continuation of application No. 13/028,557, filed on Feb. 16, 2011, now abandoned, which is a continuation of application No. 12/618,582, filed on Nov. 13, 2009, now abandoned, which is a continuation of application No. 11/352,028, filed on Feb. 10, 2006, now abandoned.

(51) Int. Cl.
*G06Q 50/24* (2012.01)
*G06Q 50/22* (2018.01)
*G06Q 10/10* (2012.01)
*G16H 50/30* (2018.01)

(52) U.S. Cl.
CPC ............. *G06Q 50/24* (2013.01); *G06Q 10/10* (2013.01); *G06Q 50/22* (2013.01); *G16H 50/30* (2018.01)

(58) Field of Classification Search
CPC .. G06Q 50/22; G06Q 50/24; G06Q 10/06398; G06Q 10/10; G16H 50/30
USPC ........................................................ 705/2–3
See application file for complete search history.

(56) References Cited

U.S. PATENT DOCUMENTS

| 6,014,629 A | 1/2000 | DeBruin-Ashton |
| 6,067,524 A | 5/2000 | Byerly |
| 6,240,394 B1 | 5/2001 | Uecker |

(Continued)

OTHER PUBLICATIONS

WayBackMachine, www.coastlineelderly.org, Jun. 18, 2004—Index.htm, Mission.htm, Info.htm, Services.htm, Shine.htm.

(Continued)

*Primary Examiner* — Joy Chng
(74) *Attorney, Agent, or Firm* — Stetina Brunda Garred & Brucker

(57) ABSTRACT

A method of administering healthcare to patients with multiple integral diagnoses such that the clinical outcomes and health-related quality of life of said patients are improved while medical costs are minimized. A patient population is first identified. The population is then stratified into specific levels of intervention. Each individual patient is then assigned a Priority Care Nurse Manager who serves to establish communication between the patient, the patient's Primary Care Physician, and any healthcare providers. The most appropriate treatment plan is cooperatively developed and the patient receives treatment according to the plan. The most appropriate treatment may include home care and palliative measures. The patient may appoint a Health Care Agent to make medical decisions for the patient should the patient be unable to make decisions.

4 Claims, 1 Drawing Sheet

(56) References Cited

U.S. PATENT DOCUMENTS

| | | |
|---|---|---|
| 6,263,330 B1 | 7/2001 | Bessett |
| 6,283,761 B1 | 9/2001 | Joao |
| 6,298,348 B1 | 10/2001 | Eldering |
| 6,341,265 B1 | 1/2002 | Provost |
| 6,343,271 B1 | 1/2002 | Peterson et al. |
| 6,735,569 B1 | 5/2004 | Wizig |
| 6,802,810 B2 | 10/2004 | Ciarniello et al. |
| 6,820,058 B2 | 11/2004 | Wood et al. |
| 6,824,052 B2 | 11/2004 | Walsh |
| 7,016,856 B1 | 4/2006 | Wiggins |
| 7,039,458 B2 | 5/2006 | Ueda et al. |
| 7,251,610 B2 | 7/2007 | Alban et al. |
| 7,275,220 B2 | 9/2007 | Brummel et al. |
| 7,464,041 B2 | 12/2008 | Merkin |
| 7,483,838 B1 | 1/2009 | Marks |
| 7,490,048 B2 | 2/2009 | Joao |
| 7,533,353 B2 | 5/2009 | Dvorak et al. |
| 7,657,442 B2 | 2/2010 | Merkin |
| 7,698,154 B2 | 4/2010 | Marchosky |
| 7,702,524 B1 | 4/2010 | Whibbs et al. |
| 7,734,656 B2 | 6/2010 | Bessette et al. |
| 7,742,930 B1 | 6/2010 | Calhoun, Jr. et al. |
| 7,801,744 B2 | 9/2010 | Patterson |
| 7,856,456 B2 | 12/2010 | Bessette |
| 7,881,950 B2 | 2/2011 | Petterson |
| 7,899,689 B1 | 3/2011 | Wizig |
| 7,904,313 B2 | 3/2011 | Knight |
| 7,917,438 B2 | 3/2011 | Kennedy et al. |
| 7,958,002 B2 | 6/2011 | Bost |
| 7,984,079 B2 | 7/2011 | Bessette |
| 8,050,945 B2 | 11/2011 | Patterson |
| 8,060,376 B2 | 11/2011 | Horner |
| 8,262,394 B2 | 9/2012 | Walker et al. |
| 8,285,565 B2 | 10/2012 | Kerr et al. |
| 8,289,750 B2 | 10/2012 | Krishnan et al. |
| 8,290,789 B2 | 10/2012 | Wennberg |
| 8,296,333 B2 | 10/2012 | Bessette |
| 8,308,062 B1 | 11/2012 | Walton, III |
| 8,311,855 B2 | 11/2012 | Kerr et al. |
| 8,321,239 B2 | 11/2012 | Hansen et al. |
| 8,326,648 B2 | 12/2012 | Kennedy et al. |
| 8,332,466 B1 | 12/2012 | Cha et al. |
| 8,335,696 B2 | 12/2012 | Brown |
| 8,380,631 B2 | 2/2013 | Dala et al. |
| 8,442,840 B2 | 5/2013 | Menocal et al. |
| 8,452,617 B2 | 5/2013 | Kerr et al. |
| 2001/0037214 A1 | 11/2001 | Raskin et al. |
| 2002/0000247 A1 | 1/2002 | Michelson et al. |
| 2002/0007290 A1 | 1/2002 | Gottlieb |
| 2002/0019754 A1 | 2/2002 | Peterson et al. |
| 2002/0026105 A1 | 2/2002 | Drazen |
| 2002/0035316 A1 | 3/2002 | Drazen |
| 2002/0120471 A1 | 4/2002 | Drazen |
| 2002/0062226 A1 | 5/2002 | Ito |
| 2002/0072933 A1* | 6/2002 | Vonk .................... A61B 5/0002 705/2 |
| 2002/0123906 A1 | 9/2002 | Goetzke et al. |
| 2002/0149616 A1 | 10/2002 | Gross et al. |
| 2003/0023598 A1 | 1/2003 | Janakiraman et al. |
| 2003/0060688 A1* | 3/2003 | Ciarniello ............. G06Q 40/08 600/300 |
| 2003/0074228 A1 | 4/2003 | Walsh |
| 2003/0078811 A1 | 4/2003 | Cole et al. |
| 2003/0078813 A1 | 4/2003 | Haskell et al. |
| 2003/0078911 A1 | 4/2003 | Haskell et al. |
| 2003/0167183 A1 | 9/2003 | Kido et al. |
| 2003/0167189 A1 | 9/2003 | Lutgen et al. |
| 2003/0182290 A1* | 9/2003 | Parker .................... G06Q 40/02 |
| 2003/0193448 A1 | 10/2003 | Tsui |
| 2003/0212579 A1* | 11/2003 | Brown .................. A61B 5/411 705/2 |
| 2004/0035434 A1* | 2/2004 | Easter .................... A61B 90/00 128/898 |
| 2004/0044546 A1* | 3/2004 | Moore .................. G06F 19/325 705/2 |
| 2004/0103022 A1 | 5/2004 | Chilcoat, III et al. |
| 2004/0186744 A1 | 9/2004 | Lux |
| 2005/0091077 A1 | 4/2005 | Reynolds |
| 2005/0202383 A1* | 9/2005 | Thomas ................. G06Q 50/22 434/262 |
| 2006/0080146 A1 | 4/2006 | Cook et al. |
| 2006/0085222 A1 | 4/2006 | Huang et al. |
| 2007/0122783 A1 | 5/2007 | Habashi |
| 2007/0203760 A1 | 8/2007 | Schmidt et al. |
| 2007/0244714 A1 | 10/2007 | McCluskey et al. |
| 2008/0059224 A1 | 3/2008 | Schechter |
| 2008/0086327 A1 | 4/2008 | Cox et al. |
| 2009/0024417 A1 | 1/2009 | Marks et al. |
| 2009/0113008 A1 | 4/2009 | Gonzalez et al. |
| 2009/0254375 A1 | 10/2009 | Martinez et al. |
| 2010/0131298 A1 | 5/2010 | Buttner et al. |
| 2010/0028085 A1 | 11/2010 | Merkin |
| 2011/0145018 A1 | 6/2011 | Fotsch et al. |
| 2011/0153348 A1 | 6/2011 | Kerr et al. |
| 2011/0270632 A1 | 11/2011 | Manning et al. |
| 2012/0191472 A1 | 7/2012 | Thesman |
| 2012/0191487 A1 | 7/2012 | Merkin |
| 2012/0226507 A1 | 9/2012 | Wendt |
| 2012/0278094 A1 | 11/2012 | Kovacevic et al. |
| 2012/0284044 A1 | 11/2012 | Bregante et al. |
| 2012/0284055 A1 | 11/2012 | Hansan et al. |
| 2012/0284056 A1 | 11/2012 | Hofstetter |
| 2012/0284057 A1 | 11/2012 | Hansan et al. |
| 2012/0290322 A1 | 11/2012 | Bergman et al. |
| 2012/0296665 A1 | 11/2012 | Merkin |
| 2012/0303381 A1 | 11/2012 | Bessette |
| 2012/0329015 A1 | 12/2012 | Thesman |
| 2013/0030838 A1 | 1/2013 | Myers et al. |
| 2013/0041690 A1 | 2/2013 | Brough |
| 2013/0124226 A1 | 5/2013 | Gedala |

OTHER PUBLICATIONS

Gibson, James L. et al.; Organizations: Behavior Structure Processes; 9th Edition, Times Mirror Higher Education Group; Chapter 7; 1997; pp. 176-191.

Grossman, Claudia, et al.; Chapter 5—Healthcare Data as a Public Good; Privacy and Security Clinical Data as the Basic Staple of Health Learning; Creating and Protecting a Public Good; Workshop Summary; 2010; pp. 171-202; The National Academies Press; Washington, DC.

* cited by examiner

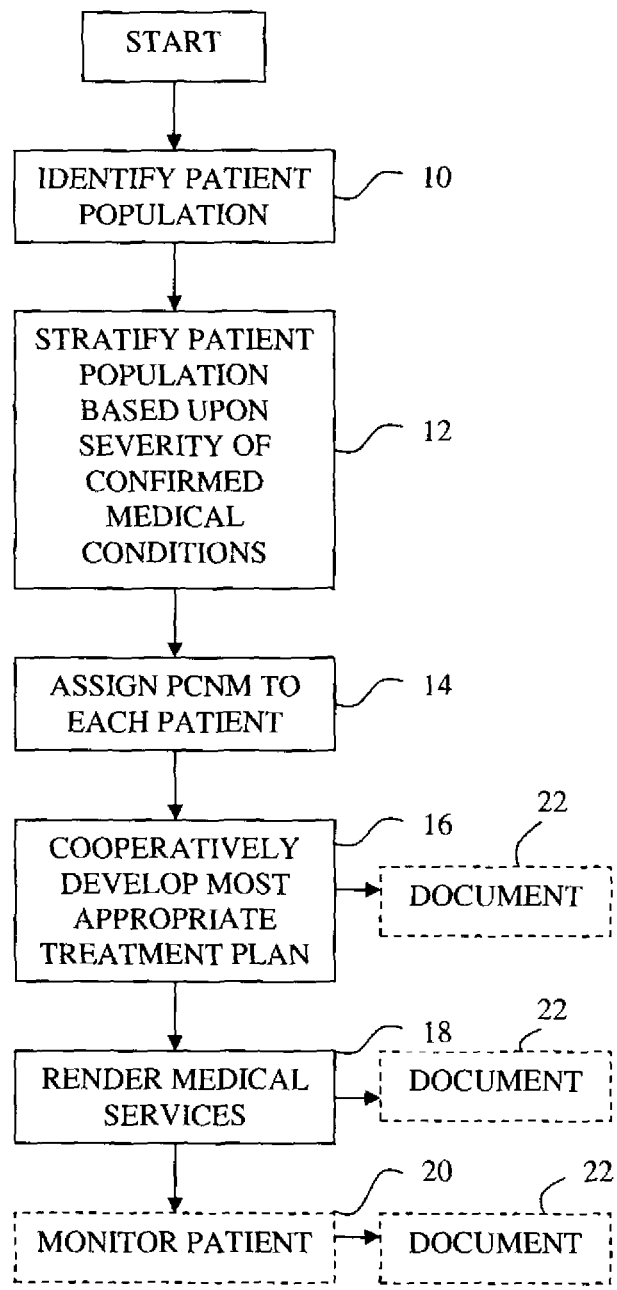

SYSTEM AND METHOD OF PRIORITIZING AND ADMINISTERING HEALTHCARE TO PATIENTS HAVING MULTIPLE INTEGRAL DIAGNOSES

CROSS-REFERENCE TO RELATED APPLICATIONS

The present application is a continuation of U.S. patent application Ser. No. 13/754,693, filed Jan. 30, 2013, entitled SYSTEM AND METHOD OF PRIORITIZING AND ADMINISTERING HEALTHCARE TO PATIENTS HAVING MULTIPLE INTEGRAL DIAGNOSES, which is a continuation of U.S. patent application Ser. No. 13/439,565, filed Apr. 4, 2012, entitled SYSTEM AND METHOD OF PRIORITIZING AND ADMINISTERING HEALTHCARE TO PATIENTS HAVING MULTIPLE INTEGRAL DIAGNOSES, which is a continuation of U.S. patent application Ser. No. 13/028,557, filed Feb. 16, 2011, entitled SYSTEM AND METHOD OF PRIORITIZING AND ADMINISTERING HEALTHCARE TO PATIENTS HAVING MULTIPLE INTEGRAL DIAGNOSES, which is a continuation of U.S. patent application Ser. No. 12/618,582, filed Nov. 13, 2009, entitled SYSTEM AND METHOD OF PRIORITIZING AND ADMINISTERING HEALTHCARE TO PATIENTS HAVING MULTIPLE INTEGRAL DIAGNOSES, which is a continuation of U.S. patent application Ser. No. 11/352,028, filed Feb. 10, 2006 entitled SYSTEM AND METHOD OF PRIORITIZING AND ADMINISTERING HEALTHCARE TO PATIENTS HAVING MULTIPLE INTEGRAL DIAGNOSES, all of the teachings of which are incorporated herein by reference.

STATEMENT RE: FEDERALLY SPONSORED RESEARCH/DEVELOPMENT

Not Applicable

BACKGROUND

The present invention is directed to systems and methods for administering healthcare resources amongst patients within a patient population. More particularly, the present invention comprises systems and methods for prioritizing treatment of patients having multiple integral diagnoses based on the severity of confirmed medical conditions.

The ability to render high quality healthcare in a cost effective manner is an elusive object that many healthcare plans and providers have attempted but few have actually attained. Despite substantial efforts made by healthcare plans, health maintenance organizations (HMO), physician networks, government-sponsored health care plans and the like, there is lacking a system for facilitating healthcare treatment for patients with multiple integral diagnoses, wherein the patients' quality of life is improved while at the same time medical costs are minimized in order to be able to provide the best care to the most patients.

It is well known that patients with multiple integral diagnoses face poor clinical outcomes and a low quality of life that is further exacerbated by the patient not abiding by the prescribed treatment plan. Also, many patients with multiple integral diagnoses are not fully educated as to all of the options available to them within their medical plan coverage and accordingly do not avail themselves of all possibilities for treatment of their conditions. Furthermore, under traditional healthcare plans, different members of a patient's health care team are often unaware of each other's activities and of the patient's overall treatment plan. As such, oftentimes a patient with multiple integral diagnoses that if carefully managed would be able to vastly improve her clinical outcome and health-related quality of life suffers due to lack of maintaining a developed treatment plan, lack of education, and/or lack of healthcare team coordination. Additionally, medical costs are often wasted due to this lack of coordination and lack of educating the patient to all possibilities for treatment causing an overall loss in funds available for treatment of the entire patient population.

For example, many patients with multiple integral diagnoses are unaware of the possibility of avoiding hospitalization and extreme life sustaining treatments. It has been assumed that the treatment of disease includes hospitalizing the patient and taking all measures necessary in order to prolong the life of the patient, irregardless of what that patient's quality of life will be. Traditional healthcare plans often do not focus on what may be the best option for the patient, or do not take the patient's desires into consideration when reaching a medical treatment plan.

As such, there is a substantial need in the art for a healthcare administration system and method that are operative to effectively and efficiently utilize healthcare resources to administer care to patients with multiple integral diagnoses. There is further a need in the art for such a system and method that serves to improve the patient's clinical outcome and quality of life while minimizing medical expenses.

BRIEF SUMMARY

The present method is directed to methods of administering healthcare to patients with multiple integral diagnoses such that the clinical outcomes and health-related quality of life of the patients are improved while medical costs are minimized. According to a preferred embodiment, a patient population is first identified which is entitled to receive such healthcare. The patient population is then stratified into specific levels of intervention. Each patient is then assigned a Priority Care Nurse Manager (PCNM). The PCNM then establishes communication between herself, the patient's Primary Care Physician (PCP), and the patient in order to cooperatively develop the most appropriate treatment plan available to the patient. Finally, the healthcare services determined by the treatment plan are rendered to the patient.

The identified patients may be actively enrolled in a Health Maintenance Organization (HMO), a governmental health program, or some similar health plan. Patients enrolled in an HMO may be commercial patients, Medicaid patients, or Medicare Advantage patients. Governmental health programs may include Medicaid and Medicare. Further, the identified patients may have ongoing needs to maintain optimal health status. These ongoing needs may include having a chronic medical condition, having a recurring medical condition, having multiple emergency room visits within the previous year, having functional or emotional impairments, having a mental or physical handicap or a developmental disability, having a terminal illness, being an organ transplant recipient, being a pain management recipient, being dependent on medical, technological support, or having multiple surgeries or hospitalization within the previous year. Alternatively, the identified patients may have a specific condition requiring continuing treatment and monitoring. These specific conditions may include HIV/AIDS, cardiovascular conditions, multiple traumas or neurological conditions, sick neonates, obstetric conditions, or malignant cancerous conditions.

The stratification into specific levels of intervention may be based upon the severity of the patients' confirmed medical conditions. The patient population may then be divided into three specific groups based upon the confirmed severity.

The PCNM may further communicate with a specialist physician, a provider of healthcare service, a patient's family member, and/or a person designated by the patient. After receiving the patient's consent, it may be determined that the most appropriate treatment plan includes not hospitalizing the patient. The treatment plan may further include maintaining the patient at her home, an assisted living facility, or a hospice facility, forgoing aggressive life-continuing treatment, and providing palliative care.

The method may further include the PCNM periodically contacting the patient. This contact may be used to determine the patient's overall status, compliance with the established treatment plan, and to identify any needed changes in the treatment plan.

The method may include documentation of all communications. All healthcare services rendered may also be documented. Finally, the results of all periodic contact with the patient may be documented.

The method may also include the patient completing a Health Care Proxy (HCP) form. The HCP form may be used to appoint a Health Care Agent (HCA) who may make medical decisions for the patient in situations where the patient is unable to make medical decisions for herself.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 1 is a flowchart depicting the steps for practicing the present invention as it relates to administering healthcare to a population of patients afflicted with multiple integral diagnoses, including the development of the most appropriate treatment plan for each patient with the aid of a Priority Care Nurse Manager.

DETAILED DESCRIPTION

The present invention is directed to methods of effectively administering healthcare to patients with multiple integral diagnoses. To this end, such patients are enrolled in a Priority Care Management Program (PCMP). The goals of the PCMP are to improve the patients' clinical outcomes and health-related quality of life, while at the same time minimizing medical costs, by increasing patient adherence to the physician established treatment plan for the management of the patient's medical conditions. The result is decreased numbers of avoidable hospitalizations, decreased numbers of hospital readmissions, decreased numbers of Emergency Room visits, decreased patient mortality, and improved patient and physician satisfaction.

According to a preferred embodiment illustrated in FIG. 1, a patient population is first identified in step 10 which will receive this healthcare. The identification of such patient population in step 10 may be achieved by identifying patients with Multiple Integral Diagnoses (MID). Such patients are identified with chronic conditions that if carefully managed will result in improved clinical outcomes and medical cost savings. This may be achieved by analyzing claims and referral utilization data to identify patients that would qualify for the program. It is contemplated that members eligible for participation in the PCMP would be actively enrolled in a Health Maintenance Organization (HMO), a governmental health program, or some similar medical plan. In one embodiment, the PCMP would be completely voluntary and provided to the patients at no additional charge above any premiums they already pay to their individual medical plan.

Once identified in step 10, the patient population is stratified into specific levels of member interventions in step 12. This stratification is achieved by the Primary Care Physician's (PCP) and/or specialty physician's evaluation of each patient in order to determine the severity of each patient's confirmed medical condition. In a preferred embodiment, the patient population is stratified into three specific levels of member interventions based upon identified need.

Patients in the first level of case management, Low Intensity Care Management, will receive an assessment of their utilization history; a follow-up assessment with patient/caregivers regarding access to services, adherence to plan of care, safety, knowledge deficits, and outcomes; patient education concerning a review of health plan benefits, self-management skills, and awareness of signs and symptoms of impending complications; a coordinated plan of care with servicing providers; and identification of community resources offered. Patients in the second level of case management, Complex Care Management, will receive all of the focused interventions of level one along with intermittent assessments and follow-ups with patient/caregivers, physicians, and/or ancillary providers regarding access to services, adherence to plan of care, safety, knowledge deficits, and outcomes, including identification of long-term and short-terms goals; individualized and comprehensive assessment and evaluation; and facilitation and coordination of safe, appropriate, high quality, cost-effective care within the patient's health plan benefit structure. Patients in the third level of case management, High Intensity Care Management, will receive all of the focused interventions of Level 1 and 2 along with frequent assessments and follow-ups with patient/caregivers regarding access to services, adherence to plan of care, safety issues, knowledge deficits, and outcomes; and focused interventions utilizing innovative possibilities to facilitate coordination of specialized needs with an emphasis on achieving optimal outcome in the most efficient, cost-effective manner.

Each patient is then assigned a Priority Care Nurse Manager (PCNM) in step 14 who will oversee the patient's individual treatment plan. The PCNM will contact the patient and/or family members to introduce the program and will then establish contact with the healthcare team treating the patient in regards to the patient's medical status and treatment plan. The healthcare team may consist of the PCP, physician specialists, and/or providers of service. In step 16, the PCNM communicates and collaborates, as is necessary, with the patient, the patient's physicians, the patient's providers, the patient's family members, and/or anyone designated by the patient in order to develop the most appropriate treatment plan that is available to the patient. The PCNM will then proceed in step 18 to coordinate and facilitate implementation of all required services. In optional step 20, the PCNM may periodically monitor the patient's overall status, adherence to the established treatment plan and any needed changes in the treatment plan in order to ensure that the patient is taking full advantage of the healthcare benefits available under the patient's health plan. All interactions involving the PCNM, any requests for services, and all healthcare services actually rendered may be documented by the PCNM in optional step 22. Priority Care Nurse Management rounds may be conducted weekly in which patient files will be reviewed by senior management with the PCNM in order to determine that the optimal level of care is being used.

Patients eligible for participation in the PCMP may have ongoing needs to maintain optimal health status, including but not limited to chronic conditions; recurring medical conditions; multiple emergency room visits, surgeries, or hospitalizations in the prior year; functional or emotional impairments; mental, physical, or developmental disablements; terminal illness; an organ transplant recipient; a pain management patient; or being dependent on medical, technological support (such as ventilator dependency). Chronic conditions may include but are not limited to asthma, congestive heart failure, chronic obstructive pulmonary disease, diabetes, and end stage renal disease.

Alternatively or additionally, patients eligible for participation in the PCMP may have specific conditions or diagnoses, including but not limited to HIV/AIDS; cardiovascular conditions; multiple trauma or neurological conditions; sick babies or neonates; obstetric conditions; or malignant cancerous conditions. HIV/AIDS may include but is not limited to HIV/AIDS with *Pneumocystis carinii* pneumonia; HIV/AIDS with Kaposis Sarcoma; or HIV/AIDS with pneumonia from an unspecified organism. Cardiovascular conditions may include but are not limited to aortic rupture, ruptured abdominal aneurysm, diseases of the aortic or mitral valve, arrhythmias, atrial fibrillation, ventricular fibrillation, paroxysmal atrial tachycardia, premature ventricular contractions, tachycardia, bradycardia, cardiac arrest, cardiac ischemia, coronary artery disease, endocarditis, perforated heart, myocardial infarction, intractable angina, peripheral vascular disease, or cardiac bypass surgery. Multiple trauma or neurological conditions may include but are not limited to altered mental status, brain aneurysm, brain tumor, paraplegia, quadriplegia, multiple sclerosis, cerebral anoxia/hypoxemia, cerebral atherosclerosis, coma, a cerebral vascular accident or hemorrhage, a motor vehicle accident or multiple trauma, transient ischemic attacks, unconsciousness, anoxic encephalopathy, hydrocephalus, closed head injury, spinal cord injury, burns, frostbite, amputations, meningitis, Reyes Syndrome, Guillian Barre, amyotropic lateral sclerosis (ALS), Alzheimer's disease, or primary dementia. The cerebral vascular accident or hemorrhage may include intracerebral, intracranial, subdural or unspecified incidents. A motor vehicle accident may include automobile versus motorcyclist, pedestrian versus automobile, cardiac injury including cardiac contusions, fractured skull, crush injuries, and shock. Sick babies or neonates may include but are not limited to anemic newborns, respiratory arrest (apnea newborns), premature births, birth traumas, or congenital anomalies (major or multiple). Obstetric conditions may include but are not limited to pregnancy with three or more fetuses, bleeding during pregnancy, history of problem births or sick babies, or toxemia during pregnancy which requires hospitalization. Malignant cancerous conditions may include but are not limited to unspecified cancers, brain cancers, bone metastasis, colon cancer, esophageal cancer, kidney cancer, liver cancer, lung cancer, ovarian cancer, prostate cancer, spinal cancer, stomach cancer, leukemia, lymphatic cancer, aplastic anemia, lymphoma, malignant leucopenia, unspecified metastasis, specified metastasis, myeloma, or other conditions which require chemotherapy and/or radiation therapy.

It is contemplated by this invention that in some situations the most appropriate level of care for a patient identified in step 16 may be to avoid hospitalization. In this regard, the present invention may include the utilization of a Do Not Resuscitate (DNR) order and/or a Do Not Hospitalize (DNH) order. It is human nature to want to send a sick person to the hospital; however, that may not always be in the best interest of the patient. That does not mean that the patient receives no care; rather, the focus of the care is on providing relief from uncomfortable symptoms while at the same time not unnecessarily prolonging what will be a short, painful remainder of life. In some cases, the best possible care determined in step 16 may include maintaining the patient at home, in an assisted living facility, an inpatient skilled nursing facility, or a hospice facility. In such cases, all efforts will be made to keep the patient free of pain and allow for a peaceful end.

Additionally, the present invention may include the utilization of a living will and/or a Health Care Proxy (HCP). As used herein, a living will means a document in which the patient identifies the types of treatment the patient does and does not desire in the case that the patient can no longer speak for herself. As used herein, an HCP is a document wherein a patient designates a Health Care Agent (HCA) who will make medical decisions for the patient in the case that the patient is no longer capable of making her own health care decisions. For the purposes of this invention, a patient is no longer capable of making their own medical decisions when the treating doctor determines that the patient is no longer able to make such decisions and another healthcare professional agrees that this is true. The HCA should be at least eighteen years old, made aware of the patient's wishes, and agree to respect and follow those wishes. A preferred HCA would be someone who knows the patient very well, cares about the patient, is capable of making difficult decisions, and is likely to be nearby when decisions need to be made. Depending on each patient's individual situation a spouse or family member may be the best choice, or they may be too emotionally involved to be the best choice. Regardless of whom the patient appoints as her HCA, it should not be the patient's health care provider, an employee of the patient's healthcare provider, or serving as an HCA for 10 or more people unless he or she is your spouse or close relative.

The HCP is revocable by the patient at any time by destroying all copies, informing his doctor or family that he wishes to cancel or change his HCA, or writing the word "Revoked" across the name of each agent he wants to cancel and signing that page. The HCP may also include an expiration date after which it is no longer valid. The HCA can make all medical decisions for the patient, or the patient may define in the HCP which decisions may be made by the HCA. The patient may also include specific instructions in the HCP regarding certain medical treatments, if so desired. These treatments may include, but are not limited to the following items: artificial respiration, artificial nutrition and hydration, cardiopulmonary resuscitation (CPR), antipsychotic medication, electric shock therapy, antibiotics, surgical procedures, dialysis, transplantations, blood transfusions, abortion, and sterilization. For example, an HCP may include directions that the patient does not want to be in pain so that the doctor should deliver enough medicine to relieve the pain even if the result is making the patient drowsier or sleepier than would otherwise be the case; whether the patient does not want anything done or omitted with the intention of taking your life; or that you want to be offered food and fluids only by mouth and kept clean and warm. The HCA must follow all directions made by the patient. Certain benefits of appointing an HCA include allowing the agent to make health care decisions on the patient's behalf as the patient would want them decided, choosing one person to make the decisions because the patient believes that person would make the best decisions, and choosing one person to make the decisions in order to avoid conflict or confusion between family members. An alternative HCA may also be appointed in the HCP should the primary HCA be unavailable, unable, or unwilling to make a decision. Also, the HCP may include the patient's organ and tissue donation wishes, including whether donations may be used for transplantation, research, and/or educational purposes. However, the lack of donation instructions in an HCP will not be taken to mean that the patient does not want to be an organ/tissue donor.

The above description is given by way of example, and not limitation. Given the above disclosure, one skilled in the art could devise variations that are within the scope and spirit of the invention disclosed herein. For example, it is contemplated that the invention as disclosed herein could readily be used and integrated within those systems and methods disclosed in pending U.S. patent application Ser. No. 10/615,640, filed Jun. 8, 2003, entitled HEALTHCARE ADMINISTRATION METHOD; U.S. patent application Ser. No. 10/679,178, filed Oct. 3, 2003, entitled HEALTHCARE ADMINISTRATION METHOD HAVING QUALITY ASSURANCE and U.S. patent application Ser. No. 11/063,268, filed Feb. 22, 2005, entitled SYSTEMS AND METHODS FOR ASSESSING AND OPTIMIZING HEALTHCARE ADMINISTRATION, the teachings of all of which are expressly incorporated herein by reference. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A method of identifying and administering healthcare to patients with multiple integral diagnoses, the method comprising the steps:
    a) providing at least two computer terminals;
    b) connecting the at least two computer terminals by a secure network;
    c) providing at least one database accessible by the at least two computer terminals over the secure network;
    d) providing a medical record transfer and review application accessible by the at least two computer terminals over the secure network, the medical record transfer and review application in communication with the at least one database;
    e) obtaining healthcare information for a plurality of patients, and storing said healthcare information in electronic medical records in the at least one database using the medical record transfer and review application, the electronic medical record for each individual patient defining one or more treating physicians associated with the treatment of that individual patient and including a claims history tracking each event for which medical care was rendered, the patient's case management, pharmacy information related to all medications prescribed to the patient, and all laboratory tests and results therefrom, including the specific dates that such procedures and tests were performed and medications prescribed;
    f) making the electronic medical records stored in the at least one database accessible over the Internet via a secure web-based system;
    g) assigning a standardized diagnostic code, or a set of codes, to the electronic medical records of each patient of said plurality of patients with a diagnosis of two or more confirmed medical conditions selected from the group consisting of HIV/AIDS, aortic rupture, arrhythmias, coronary artery disease, perforated heart, myocardia infarction, closed head injury, spinal cord injury, amyotrophic lateral sclerosis, apnea newborns, major or multiple congenital anomalies, brain cancers, bone metastasis, kidney cancer, lung cancer, prostate cancer, lymphoma, and unspecified metastasis,
    h) determining a patient population by the medical record transfer and review application reviewing the electronic medical records of the at least one database wherein each patient within said patient population has two or more confirmed medical conditions;
    i) rendering medical services to each patient within said patient population, the medical services comprising one or more treatments selected from the group consisting of: artificial respiration, artificial nutrition and hydration, cardiopulmonary resuscitation (CPR), antipsychotic medication, electric shock therapy, antibiotics, surgical procedure, dialysis, transplantations, blood transfusions, abortion, and sterilization;
    j) recording a plurality of medical procedure codes corresponding to the medical services rendered, the plurality of medical procedure codes being recorded in the medical record of each patient within said patient population;
    k) reviewing the plurality of medical procedure codes in the medical record of each patient within said patient population for compliance with standardized criteria of care corresponding to the two or more confirmed medical conditions of the patient, and using a statistical technique to determine discrepancies including a rate of error, the rate of error identifying improper diagnoses of a specific condition, instances of inappropriate medical procedures ordered in response to the two or more medical conditions, instances of orders for a wrong or unnecessary test in response to the two or more medical conditions, and instances of prescribing medication that is either inappropriate, sub-therapeutic or improperly indicated to treat either or both of the two or more medical conditions; and
    l) compiling data on the discrepancies and using the data to compile and adjust a corresponding series of computer-presented pertinent clinical questions specific for each chronic condition of each patient within said patient population.

2. The method of claim 1, wherein the standardized diagnostic codes are drawn from ICD-9-CM or HCC.

3. The method of claim 2, wherein the plurality of medical procedure codes are drawn from CPT codes and HCPCS codes.

4. The method of claim 2, wherein the standardized criteria of care is a list of procedures represented by standardized procedure codes.

* * * * *